(12) United States Patent
Cooper (10) Patent No.: US 6,387,081 B1
(45) Date of Patent: May 14, 2002

(54) MISTING APPARATUS FOR APPLICATION OF COATING MATERIALS TO SKIN SURFACE

(75) Inventor: Troy H. Cooper, Addison, TX (US)

(73) Assignee: Mystic Tan, Inc., Carrollton, TX (US)

( * ) Notice: Subject to any disclaimer, the term of this patent is extended or adjusted under 35 U.S.C. 154(b) by 0 days.

(21) Appl. No.: 09/521,283

(22) Filed: Mar. 7, 2000

Related U.S. Application Data
(60) Provisional application No. 60/123,932, filed on Mar. 12, 1999, provisional application No. 60/124,652, filed on Mar. 16, 1999, provisional application No. 60/126,632, filed on Mar. 29, 1999, and provisional application No. 60/126,986, filed on Mar. 29, 1999.

(51) Int. Cl.[7] .................. A61M 35/00; A61H 33/06
(52) U.S. Cl. .................. 604/289; 604/290; 132/333; 4/525
(58) Field of Search ...................... 424/401, 405, 424/400; 132/320, 333; 604/19, 289, 290, 209

(56) References Cited

U.S. PATENT DOCUMENTS

| | | | |
|---|---|---|---|
| 4,688,518 A | 8/1987 | Missier | 118/626 |
| 5,268,166 A | 12/1993 | Barnett et al. | 424/47 |
| 5,277,713 A | 1/1994 | Gelain et al. | 118/634 |
| 5,322,684 A | 6/1994 | Barnett et al. | 424/47 |
| 5,494,674 A | 2/1996 | Barnett et al. | 424/401 |
| 5,527,564 A | 6/1996 | Napadow et al. | 427/477 |
| 5,664,593 A | 9/1997 | McClain | 132/333 |
| 5,765,761 A | 6/1998 | Law et al. | 239/690.1 |
| 5,833,751 A | 11/1998 | Tucker | 118/64 |
| 5,863,497 A | 1/1999 | Dirksing | 422/28 |
| 5,922,333 A | 7/1999 | Laughlin | 424/401 |
| 6,302,122 B1 | 10/2001 | Parker et al. | 132/333 |

FOREIGN PATENT DOCUMENTS

| | | |
|---|---|---|
| EP | B 031649 | 11/1980 |
| EP | A 031649 | 11/1980 |
| EP | B 441501 | 1/1991 |
| EP | A 441501 | 1/1991 |
| EP | B 468736 | 7/1991 |
| EP | A 468736 | 7/1991 |

OTHER PUBLICATIONS
International Search Report dated Jun. 15, 2000 for PCT/US00/05854.

*Primary Examiner*—Kim M. Lewis
(74) *Attorney, Agent, or Firm*—Jenkens & Gilchrist (57) ABSTRACT

Disclosed is an apparatus and method for electrostatically coating a human with a coating composition. In one embodiment, the present invention includes an enclosure; a mount positioned on the enclosure; an electrostatic nozzle connected to the mount, the electrostatic nozzle for passing the coating composition; and a grounding connection positioned inside the enclosure, the grounding connection capable of electrically grounding the human; wherein the coating composition passed through the electrostatic nozzle is depositable upon the human. Furthermore, in another embodiment, the enclosure includes a first wall wherein the mount is positioned on the first wall; and a second wall positioned substantially opposite the first wall, the second wall including a portion curved about an axis.

40 Claims, 8 Drawing Sheets

MISTING APPARATUS FOR APPLICATION OF COATING MATERIALS TO SKIN SURFACE

RELATED APPLICATIONS

Priority is claimed to the following applications: Ser. No. 60/123,932, filed Mar. 12, 1999 (Electrostatic Misting Booth For Application Of Coating Materials To Skin Surface); Ser. No. 60/124,652, filed Mar. 16, 1999 (Electrostatic Misting Booth And Misting Apparatus For Application Of Coating Materials To Skin Surface); Ser. No. 60/126,632, filed Mar. 29, 1999 (Electrostatic Misting Booth With Vertical Moving Nozzles For Application Of Coating Materials To Skin Surface); and Ser. No. 60/126,986, filed Mar. 29, 1999 (Electrostatic Misting Booth And Misting Apparatus With Vertical Moving Nozzles For Application Of Coating Materials To Skin Surface)

BACKGROUND OF THE INVENTION

1. Field of the Invention

The present invention relates to a system for delivering skin coating chemical compositions directly to the skin. More particularly, the invention relates to methods and apparatus for applying such coatings onto the skin using a principal of electrostatic misting.

2. Background of the Invention

Conventional skin coating products, whether designed for cosmetic, treatment or medical purposes, are often liquid or viscous or semi-solid products. Most of them are produced in the form of lotions or creams. These products are traditionally applied by gentle massage or rubbing-in with the fingers. These methods of application necessitate the addition of relatively large amounts of adjunct material, i.e. other than the one or more active ingredients necessary to achieve the desired result. Most of these adjunct materials are added to create an aesthetically acceptable product and act as a carrier to deliver the active agent to all parts of the skin. These known delivery systems are wasteful of cosmetic raw materials and have limited efficiency in delivering a desired active ingredient to an intended site. Control over the applied dosage is difficult and limited and the application of the product itself is often time consuming and messy.

In addition, the presence of any significant amounts of stabilizing ingredients such as surfactants, polymers, preservatives, etc, may result in the user experiencing stickiness, greasiness, and possibly irritation. This may be particularly pronounced where skin is damaged or diseased, which may make the application of a product by massage or rubbing-in particularly undesirable.

In the case of coating compositions that are typically applied over the entire body i.e. sun tan lotions, self-tanning products, or moisturizers, application by massage or rubbing-in usually requires a second individual. This is necessary because the user of the product cannot reach and evenly coat all parts of the body unassisted. This is a significant disadvantage because a large percentage of the population would not have such an individual available to apply the product to those hard to reach places.

In addition to the above-described systems for delivering skin treatment agents, there are a small number of known examples where a skin cosmetic or therapeutic active is delivered using an aerosol spray. Two such examples are sprays for sunburn and sprains or other sports injuries. However, aerosol sprays, which are well known in the art for delivering personal products, also suffer from several disadvantages. First, the types of product and active agent that lend themselves to effective aerosol spraying are limited. Second, the use of aerosols still results in significant inefficiency and waste through non-target specific application (over-spray). This over-spray results in loss of active material to the atmosphere. It also creates unwanted mists which can damage surrounding objects if the active ingredient is reactive with whatever object the mist happens to fall on. The use of aerosols to deliver skin cosmetic or therapeutic active agents is also believed to be even less efficient than conventional massage or rubbing-in delivery regimes in the context of percentage and evenness of coverage of the skin surface. Although aerosols can be used to reach many of those hard to reach areas of the body that usually require a second individual for full body application, it is still difficult for a user to achieve a good even coating over the entire body without the assistance of another individual.

The skin is, in fact, a very complex material and has many important characteristics which must be considered in the design of an optimized system for delivering cosmetic or therapeutic actives thereto. For example, skin has a multifaceted surface having both lipophilic and lipophobic character. This character allows the skin to "breathe" and release water vapor, yet function as an effective barrier against water, dirt and other unwanted materials. One particularly important physical feature of skin is its very rough surface terrain, which creates a problem in successfully applying a desired skin cosmetic or therapeutic active with complete and even coverage.

In a very different technical field, the principle of electrostatic spraying of liquid and solid materials to increase the effectiveness of applying coating materials to objects is also known. In this technique a formulation to be sprayed is raised to a relatively high electric potential in a spray nozzle to cause the formulation to atomize as a spray of electrically charged droplets. Such electrically charged droplets seek the closest grounded object to discharge their electric charge. This can be arranged to be the desired spray target. Electrostatic spraying techniques have been proposed principally for only large-scale industrial and agricultural applications. Examples of these applications include delivering reactive materials like paints, adhesives, and other surface coatings, as well as large-scale delivery of pesticides and other agricultural or agrochemical formulations.

More recently, there have been a small number of proposals for utilizing the known principle of electrostatic spraying for delivering particular materials in specific applications other than those mentioned above. For example, EP-A-224352 (Ocular Treatment) suggests the use of an electrostatic sprayer for delivering a pharmaceutically active agent to the eye, to replace conventional ocular treatment using eye drops.

Other proposals for applying the principle of electrostatic delivery to the skin, for example, are disclosed in U.S. Pat. No. 5,268,166 (Cosmetic Application System), U.S. Pat. No. 5,494,674 (Skin Treatment System) and U.S. Pat. No. 5,322,684 (Cosmetic Delivery System). Each of these proposals suggests the same method of electrostatic spray application to coat the skin with different types of chemical compositions. In one proposal (U.S. Pat. No. 5,268,166) the coating compositions are color cosmetics, in another proposal (U.S. Pat. No. 5,494,674) the coating compositions are skin treatment agents, and in the final proposal (U.S. Pat. No. 5,322,684) the coating compositions are cosmetically active agents, such as, perfume.

In all three of the above proposals the basic application method outlined is basically the same:

(a) providing an apparatus which includes:
  (i) a reservoir containing the coating composition to be delivered which is in an electrostatically sprayable form;
  (ii) at least one delivery means which is a nozzle in communication with the reservoir;
  (iii) a high voltage generator generating voltage in the range of 2 to 20 kilovolts powered from an electricity source; and
  (iv) control means for selectively applying the high voltage from the generator to the at least one delivery means; and
(b) actuating the said control means to electrostatically spray the coating composition from the at least one delivery means directly onto the skin at an intended site.

The above proposals reference a number of possible "suitable electrostatic spraying hardware" including EP-A-441501 (Electrostatic Spraying Apparatus), EP-A-468736 (Electrostatic Spraying Device and Method), and EP-A-031649 (Containers and Holders Therefor for Use in Electrostatic Spraying). Each of these referenced electrostatic spraying devices are handheld, self contained units where the reservoir, nozzle, generator, and control for applying high voltage from the generator are in the self-contained apparatus. It is apparent from the descriptions of the "suitable electrostatic spraying hardware" that the anticipated use of the methods described in U.S. Pat. No. 5,268,166, U.S. Pat. No. 5,494,674 and U.S. Pat. No. 5,322,684 was to apply the specified coating compositions to the skin on various small, localized areas of the body (e.g., the face) by electrostatically spraying them through a handheld self-contained device.

Although this method of application offers some advantages over aerosol spraying because it would eliminate some of the over-spray problem, it is still difficult to obtain effective uniform coating over the entire body or a substantial portion of the entire body. The uniformity of the coating is impacted by the distance of the nozzle from the skin, the rate of movement of the spray over various parts of the body, the number and intensity of spray bursts necessary to cover the coating area, etc. Because every user will apply the spray differently, each of the variables will vary from user to user and from spray session to spray session. Consequently, the lack of consistency in performance will affect the consumer's acceptance of this product concept.

In another technical field, spray painting, booths have been used to contain spray mists created by air or electrostatic spray painting of objects. These booths prevent the over-spray from landing on surrounding objects that were not part of the desired target. As the art of spray painting booth has evolved one undesirable result, particularly in the case of electrostatic powder painting, has been the coating of the walls of the spray booth which requires labor and down time to clean off. This coating of the booth walls is particularly costly in electrostatic powder coating because the powder adhering to the walls cannot be effectively recycled and the cost of materials is increased.

There have been a number of proposals to resolve this problem of the booth walls being coated. U.S. Pat. No. 5,833,751 (Powder Coating Booth Having Smooth Internal Surfaces) proposes, "a powder coating booth comprising a pair of identical polycarbonate shells disposed opposite each other to define a coating chamber having smooth, curvilinear surfaces to facilitate the recovery and recycle of excess coating powder."

U.S. Pat. No. 5,277,713 (Cabin for Spray Coating Objects with Powder), for example, describes a cabin for spray coating objects with powder. In the Summary of the Invention it is specified "[w]ith the present invention, the advantages obtained are that the cabin can be produced in a very inexpensive manner, and nevertheless offers greater reliability against electrical arcing, and is electrostatically neutral, or has a repelling effect for many different kinds of powders, so that no or only a few powder particles can collect on the inner surfaces of the cabin." Moreover, U.S. Pat. No. 5,527,564 (Method and Apparatus for Repelling Overspray in Spray Paint Booths) describes a method and apparatus for repelling over-spray in spray paint booths. In the Summary of the Invention of the '564 patent, it is specified, "[a]mong its several aspects and features, the present invention provides an electrically charged panel which repels electrically charged dry or wet coating particles inside an electrostatic spray painting booth, or other booths having charged paint or powder particles therein." Later in the Detailed Description of the Preferred Embodiment of the '564 patent it is noted, "Better painting efficiency is achieved because the repelled paint particles will become available to adhere to the articles being painted".

Until recently, however, prior art in electrostatic spraying technology required that high voltage, 5 to 16 kilovolts, be generated and that the electrostatically sprayable compositions have resistivity in the range of 100,000 to 100,000,000,000 ohm centimeters. It was also recommended that the compositions either be non-aqueous or contain very small amounts of water, e.g., on the order of less than 5%. This was because an aqueous solution was difficult to spray effectively using electrostatic means due to it's low resistivity. The high voltage requirements made electrostatic spraying of coating materials on the human body too dangerous to be seriously considered. The non-aqueous solution requirement meant that the most effective and inexpensive carrier for the active coating ingredients could not be used effectively with this process.

However, recently there have been innovations in the field of electrostatic spray nozzles that have made this process more acceptable for the application of coating compositions in various fields such as industrial and agricultural applications. For example, U.S. Pat. No. 5,765,761 (Electrostatic-Induction Spray-Charging Nozzle System) and U.S. Pat. No. 5,704,554 (Electrostatic Spray Nozzles for Abrasive and Conductive Liquids in Harsh Environments) describe "air atomizing induction charging spray nozzles suitable for use with conductive liquids, solutions, suspensions or emulsions. The major advantage of the described method is the high level of spray charging that can be achieved at very low electrode voltages and power. The total power required is very low, typically less than 0.005 watts per nozzle. The introduction of this new "air-assisted induction charging system (AAIC)," which operates with low voltage and low current, makes it possible to utilize electrostatic spraying to create an electrostatic mist that could be used to apply a coating composition to the human body without the risk of any noticeable electrostatic shock.

SUMMARY OF THE INVENTION

To remedy the deficiencies of existing systems and methods, the present invention provides an apparatus for electrostatically coating a human with a coating composition. In one embodiment, the present invention includes an enclosure; a mount positioned on the enclosure; an electrostatic nozzle connected to the mount, the electrostatic nozzle for passing the coating composition; and a grounding connection positioned inside the enclosure, the grounding connection capable of electrically grounding the human;

wherein the coating composition passed through the electrostatic nozzle is depositable upon the human.

Furthermore, in another embodiment, the enclosure includes a first wall wherein the mount is positioned on the first wall; and a second wall positioned substantially opposite the first wall, the second wall including a portion curved about an axis.

BRIEF DESCRIPTION OF THE DRAWINGS

Various objects and advantages and more complete understanding of the present invention will become apparent and more readily appreciated by reference to the following Detailed Description and to the appended claims when taken in conjunction with the accompanying Drawings wherein:

FIG. 1 is a schematic view of one embodiment of the booth.

FIG. 2 is a schematic view of the operation of the booth of FIG. 1.

FIG. 3 is an expanded view of the electrostatic principles at work during operation.

FIG. 4 is a drawing of the application system.

FIG. 5 is a schematic view of a system used to provide vertical motion to the electrostatic misting nozzles.

FIG. 6 is an illustration of the application system.

FIG. 6*a* is an expanded cross sectional view of the AAIC nozzle.

FIG. 7 is a view of an alternate embodiment of a booth constructed in accordance with the principles of the present invention.

DETAILED DESCRIPTION

Although the present invention is open to various modifications and alternative constructions, a preferred exemplary embodiment that is shown in the drawings is described herein in detail. It is to be understood, however, that there is no intention to limit the invention to the particular forms disclosed. One skilled in the art can recognize that there are numerous modifications, equivalences and alternative constructions that fall within the spirit and scope of the invention as expressed in the claims.

A preferred embodiment of the present invention is illustrated in FIG. 1. The booth 1 consists of walls 2 which can be constructed of a dielectric (non-conducting) material (preferably a thermoplastic which can be thermoformed in to the desired shape), a ceiling 3 that can be constructed of the same dielectric material, a door 5 that can be constructed of the same dielectric materials as the walls and ceiling, and a floor 4 that can be made of a conducive material, preferably metal. Attached to one end of the booth 1, is a motion apparatus 6, which can be used to provide vertical (and in one embodiment horizontal) motion to at least one electrostatic nozzle 7 that is mounted to the motion apparatus 6. (In one embodiment, the electrostatic nozzle 7 is rotated/pivoted in an up-and-down direction rather than moved in a vertical direction.) Attached to the base of the wall 2 opposite the motion apparatus 6 is an exhaust housing 9 that can be opened on the end attached to the wall 2 and connected to an exhaust conduit 10. The exhaust housing 9 can be made of a dielectric material and can contain an exhaust filter 8 on the open end attached to the wall 2 and an exhaust pen 9A. When the booth 1 is in operation, a user 11 could be standing inside the booth 1, possibly, on the floor 4 that can be constructed of conductive material that can be grounded. Thus, the user 11 would also be grounded. The user could also be grounded by any other means.

Referring now to FIG. 2, there is illustrated the electrostatic misting booth 1 in operation. When the user 11 enters the booth 1 he closes the door 5 and stands at a predetermined spot, which can be at an elliptical end of the booth, as shown in FIG. 4, facing the electrostatic misting nozzle(s) 7. He could activate the system by pressing the start button 13 or by any other means. This activates a misting cycle from the electrostatic misting apparatus 12 that can be configured to deliver a specific volume of the coating composition. One example of a coating composition that might be used is a sunless tanning solution made of water (70%), dihydroxyacetone (8.75%), bronzing dye (7%), Carbopol 940 solution (4.2%), Propylene Glycol (1%), Lexorez TC-8 (3%), Octyl Palmitate (2%), and the following components in concentrations of less than 1%; Methyl Paraben, Germall II, Aloe Versa 10X, L-Tyrosine, Stearic Acid, Stearyl Alcohol, Glyceryl Monosyearate SE, Isopropyl Myristate, and Triethanolamine.

As the coating composition passes through the nozzle(s) 7 the composition is atomized into tiny droplets 15 and the droplets are charged. Because particles of like charges repel each other, once they leave the nozzle(s) 7, the droplets 15 spread into a mist. As the misting process is occurring, the nozzle(s) 7 can be moved (vertically, horizontally, or rotated) by the motion apparatus 6 to more evenly distribute the mist. Once the charged droplets 15 enter the larger space in the booth 1 they separate from each other rapidly and begin to fill the booth 1 with an electrostatic mist. The user 11 would be standing downstream of the airflow 14, and the initial force of the airflow 14 and/or the electrostatic force between the grounded user 11 and the charged droplets 15 can result in the creation of a uniform layer of the coating composition on the front side of the user 11. As the charged particles 15 move past the user 11 they lose the horizontal momentum generated by the airflow 14 of the nozzle(s) 7, and begin to succumb to the forces of gravity and descend vertically. As these excess charged droplets descend they are attracted to neutral or positively charged objects. Because the walls 2 are the first neutral object these excess droplets 15 come into contact with they can quickly begin to attach to the walls 2. Due to the dielectric nature of the walls 2 the negative charges passed on by the charged droplets 15 soon create a negative electrostatic charge 16 on the walls 2. Once this occurs the electrostatic charge 16 on the walls 2 begins to repel the remaining charged droplets that are descending. At this time the only other grounded object in the booth 1 is the grounded user 11 in the center. In an alternative embodiment, the walls 2 can be charged or coated with a charged material prior to the excess droplets 15 coming into contact with them. In this way, the walls 2 then can repel the excess droplets even more efficiently.

Now referring to FIG. 3, there is illustrated the electrostatic coating process resulting in the booth 1. Because electrostatic forces 16 are exerted perpendicular to the charged surface, the electrostatic charge on the walls 2 repels the charged droplets toward the center of the booth 1. Because the booth 1 is filled with a mist of charged droplets 15 each charged droplet 15 that is repelled from the walls exerts an electrostatic force on the charged droplet 15 next to it, thus forcing that charged droplet 15 towards the center of the booth. This process is repeated until a charged droplet 15 is close enough to the grounded user 11 at the center of the booth 1 to be attracted to him/her. Once this occurs the electrostatic forces 16 pull the charged droplet onto the skin of the grounded user and forms a thin coating. This process is continuous as the charged droplets descend downward. The result is an even layer of the coating composition over the user 11. Because the quantity of coating material on the front of the user 11 might be more than that on the backside due to the additional deposition caused by the airflow 7, the user could turn around and repeat the procedure to have an even coating over the whole body. Although, in one embodiment, the user need not turn to achieve an even coating.

Figure 1:
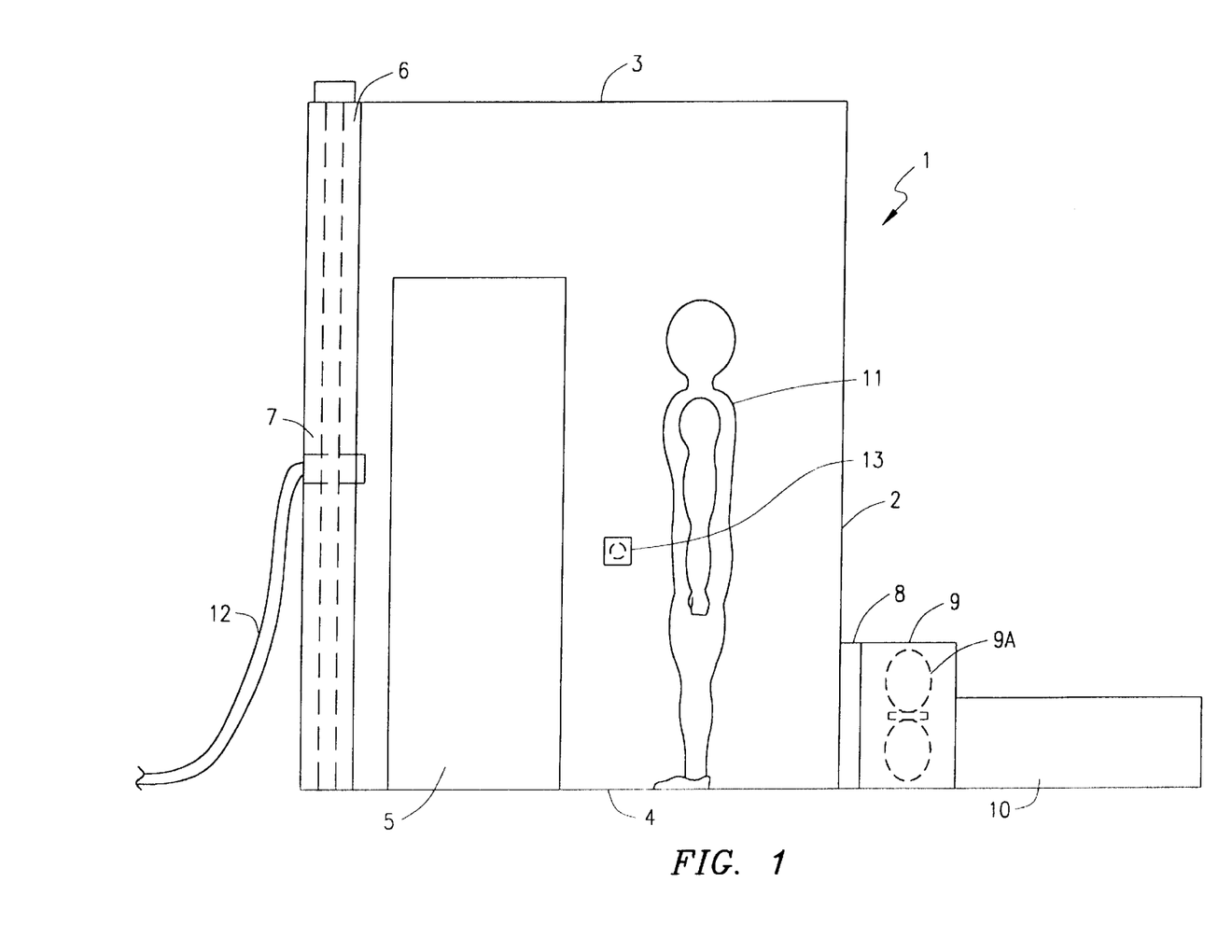
Figure 2:
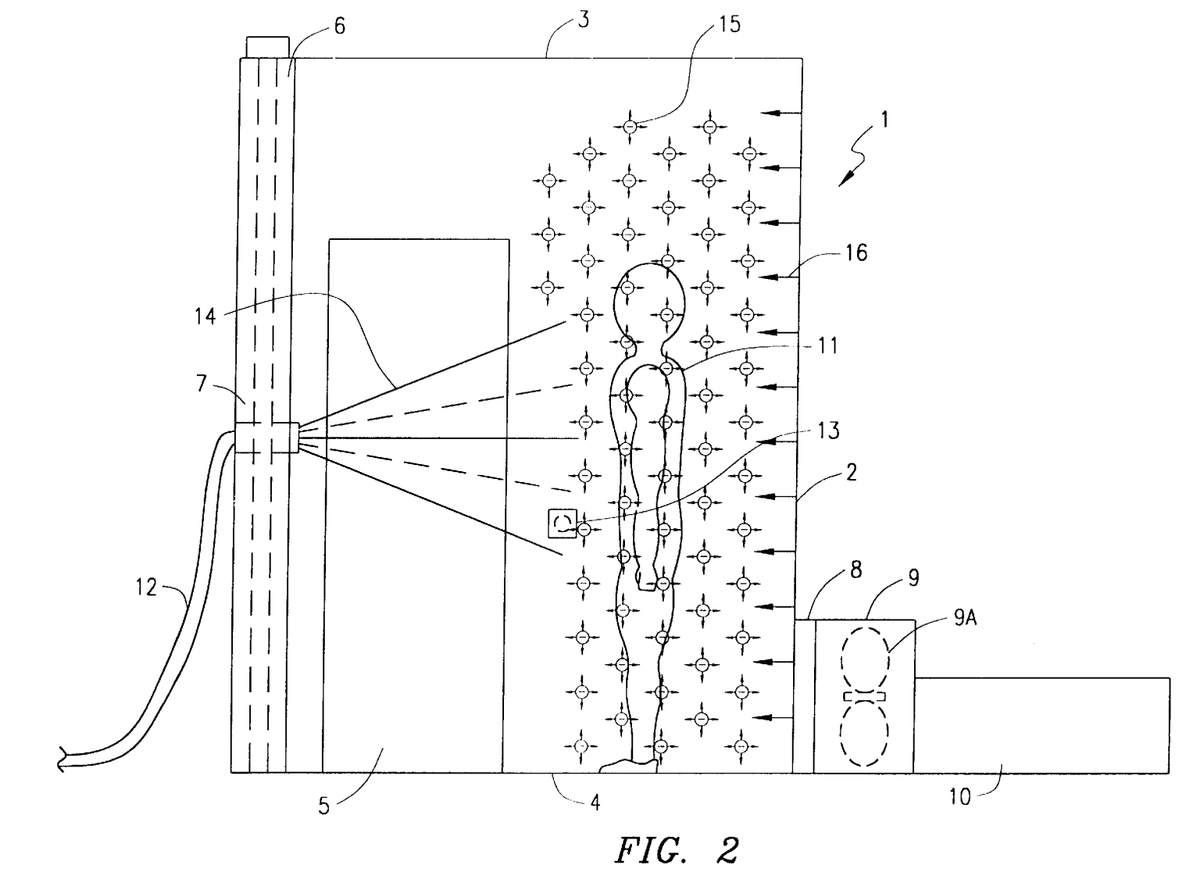
Figure 3:
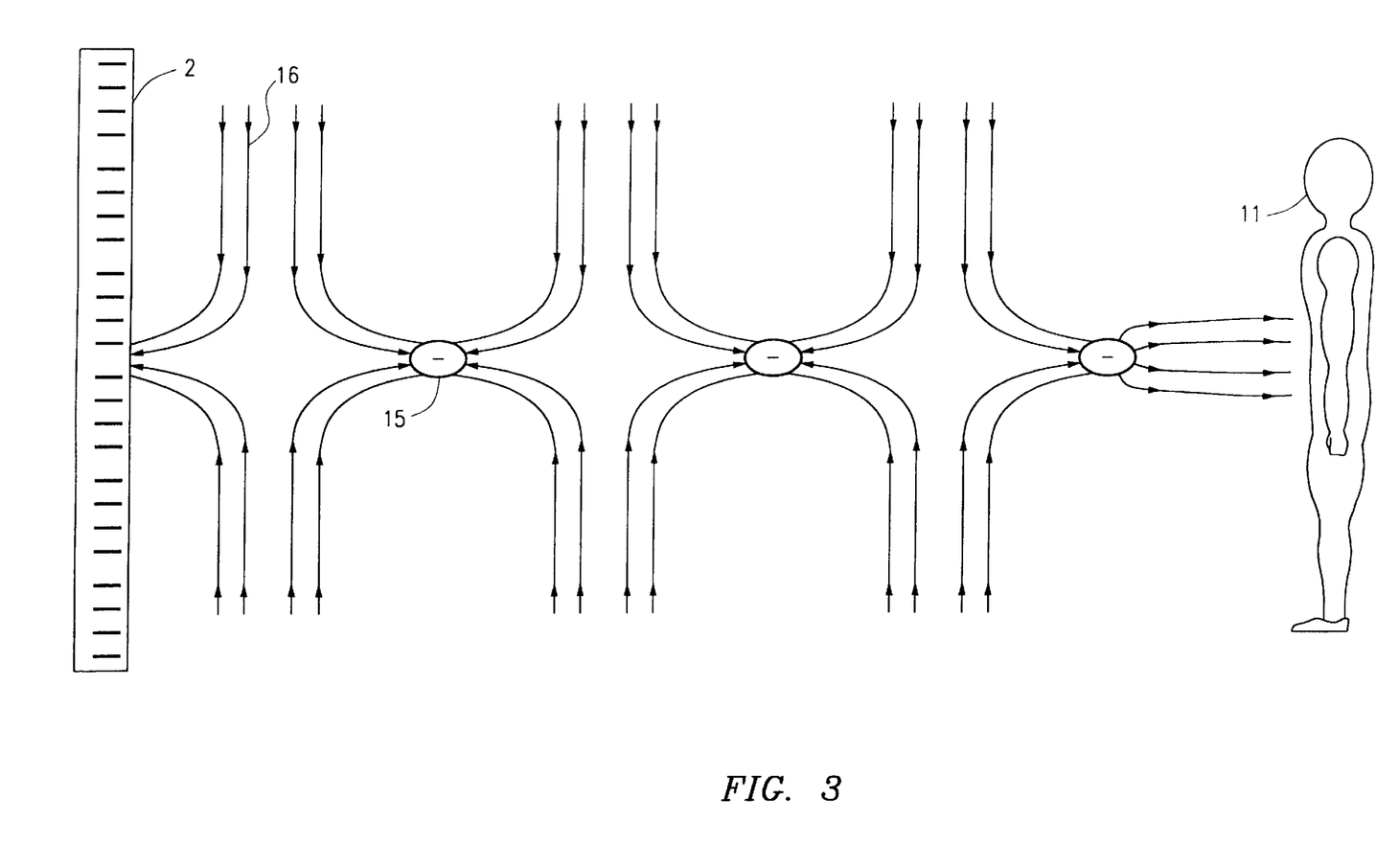

Referring back to FIG. 2, once the second coating process is complete an exhaust fan 9A starts and pulls the excess mist through a filter 8 into an exhaust conduit 10 to remove the remaining residual charged droplets 15 from the booth 1.

Figure 4:
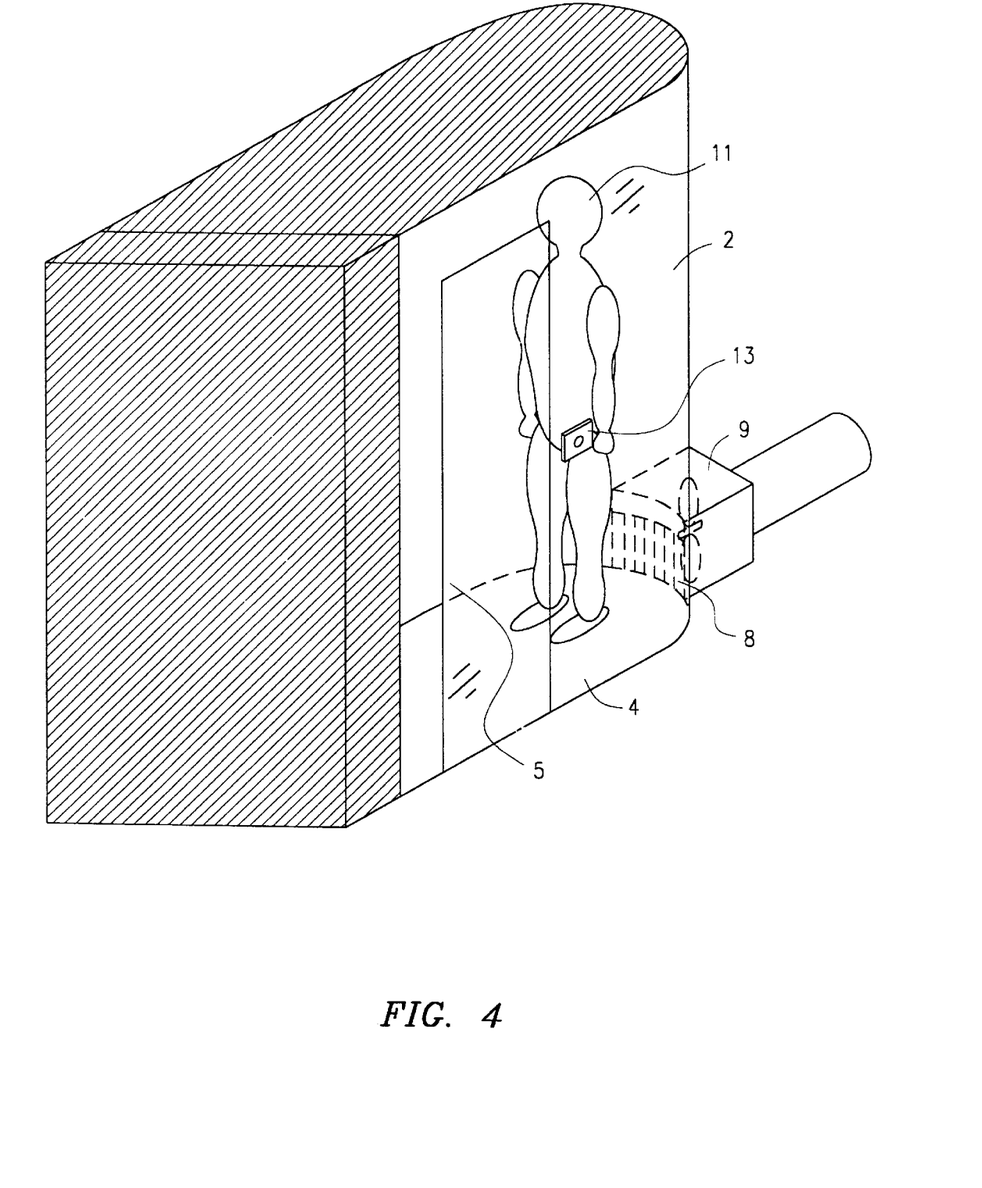

Referring now to FIG. 4, there is illustrated a view of one embodiment of the misting system at rest. This drawing illustrates that in a preferred embodiment the booth 1 walls 2 would create an elliptical shape on one end that can approximate the horizontal shape of the human body and, therefore, could be an ideal configuration for maintaining the walls 2 equidistant from the grounded user 11.

Figure 5:
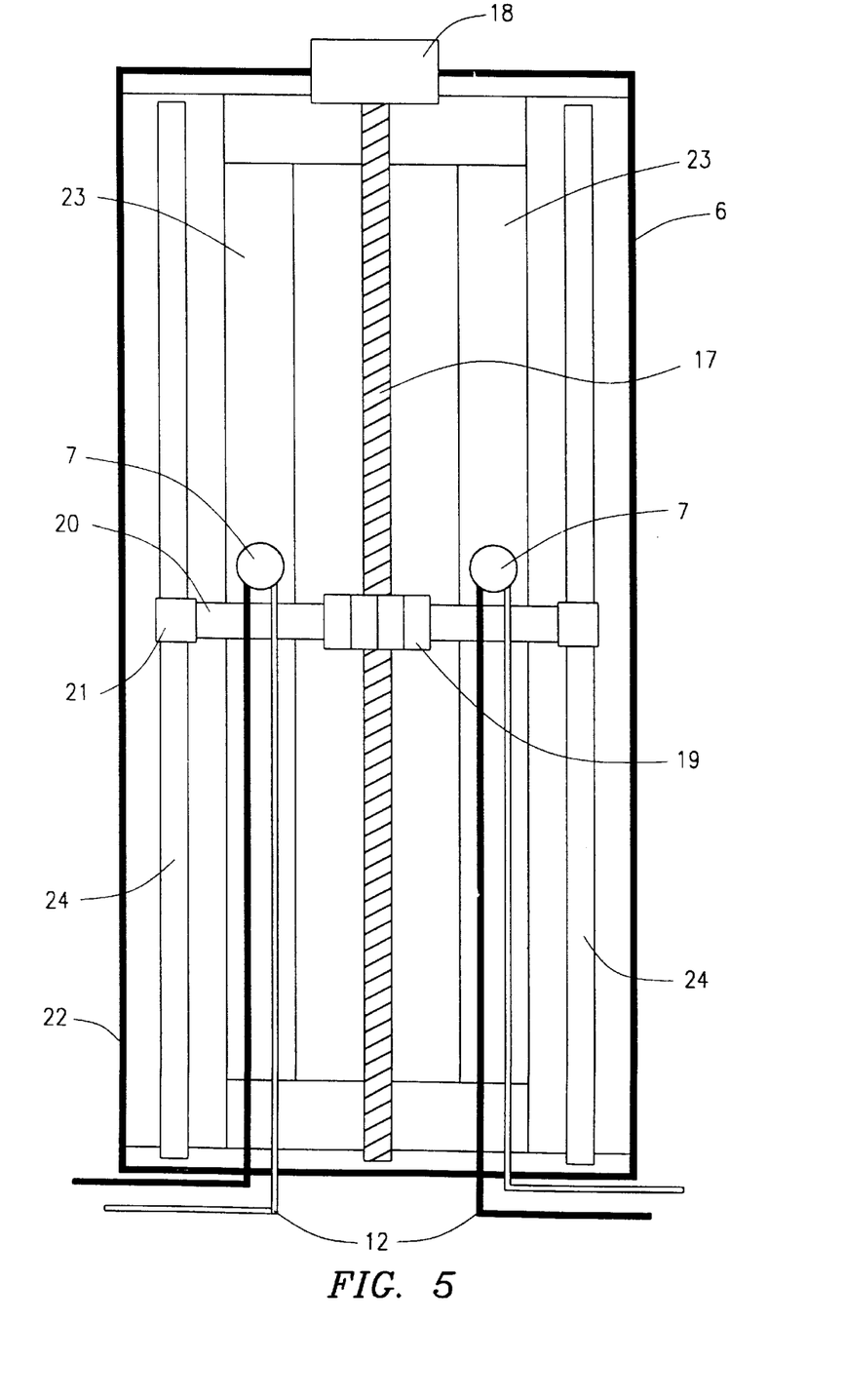

Referring now to FIG. 5, there is illustrated a view of one possible type of motion apparatus 6. In this version of the motion apparatus 6, motion is provided through a worm (screw) shaft 17, although motion can be provided in a number of ways including by a cylinder, a cable and pulley system and the like. In the embodiment including a worm shaft, when the misting cycle is activated by the user 11, the electric motor 18 attached to the worm shaft 17 begins to turn the shaft 17. As the shaft 17 turns the configuration of support bars 20, guide collars 21 and guide shafts 24 prevent the traveling nut 19 from turning thus forcing it to follow the threads up or down depending on which direction the electric motor 18 is turning the worm shaft 17. When the traveling nut 19 reaches the top most or bottom most position the direction of the electric motor 18 can be reversed by a sensor and the traveling nut 19 moves in the reverse direction. As the traveling nut 19 moves up or down the electrostatic misting nozzle(s) 7 move with it because they are attached to the support bars 20. As the misting, for example, nozzle(s) 7 move they spray electrostatic mist through the misting slots 23 located in the separation wall 22 that separates the motion apparatus 6 from the electrostatic misting booth 1.

Other types of motion apparatus 6, for example, might use pulleys and cables, compressed air, and/or hydraulic fluids to provide motion for the nozzle(s) 7. Another embodiment could merely rotate/oscillate or pivot the misting nozzles to achieve the same results.

Figure 6:
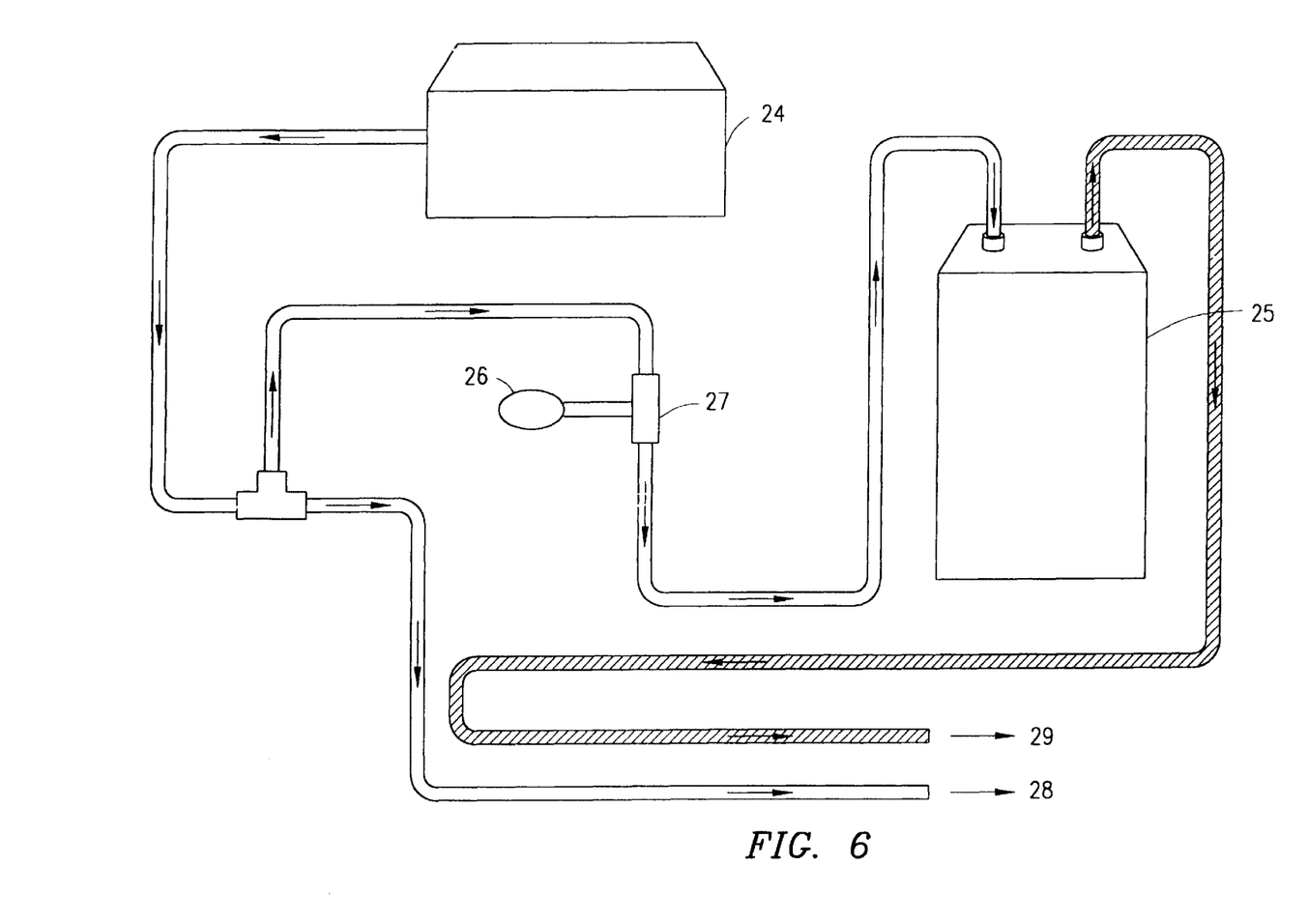
Figure 6A:
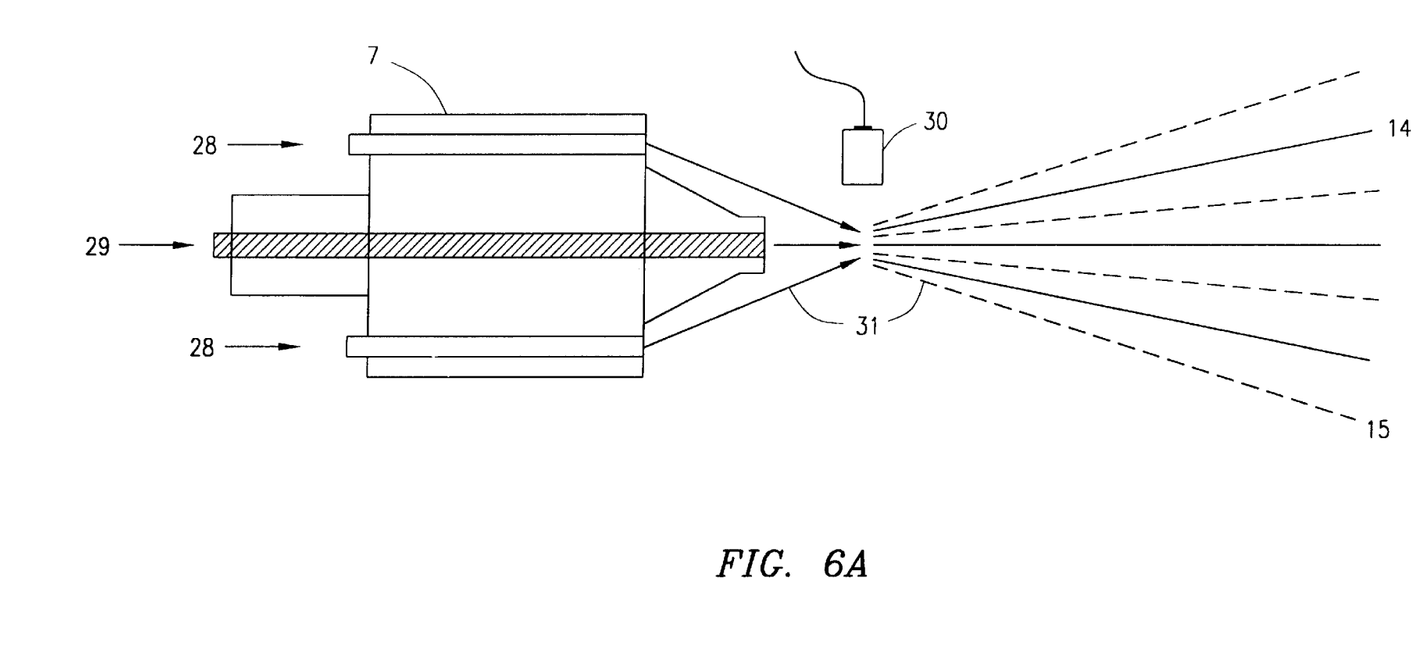

Referring now to FIG. 6, there is illustrated an isometric view of the electrostatic misting apparatus 12 consisting of an air compressor 24 which is connected to conduit that delivers the compressed air to the nozzle 7 and the coating composition reservoir 25. The coating composition reservoir 25 is connected to conduit that delivers the coating composition to the nozzle 7. The air flow 28 to the coating composition reservoir 25 is controlled by the air flow regulator 27 and monitored through the air pressure gage 26. The liquid flow 29 is generated by the air pressure in the reservoir 25 which forces the liquid out. (In an alternate embodiment, the liquid flow is generated by a liquid pump.) Moreover, FIG. 6A illustrates the electrostatic misting zone 31 where the air and liquid come together and are negatively charged by the electrode 30.

Figure 7:
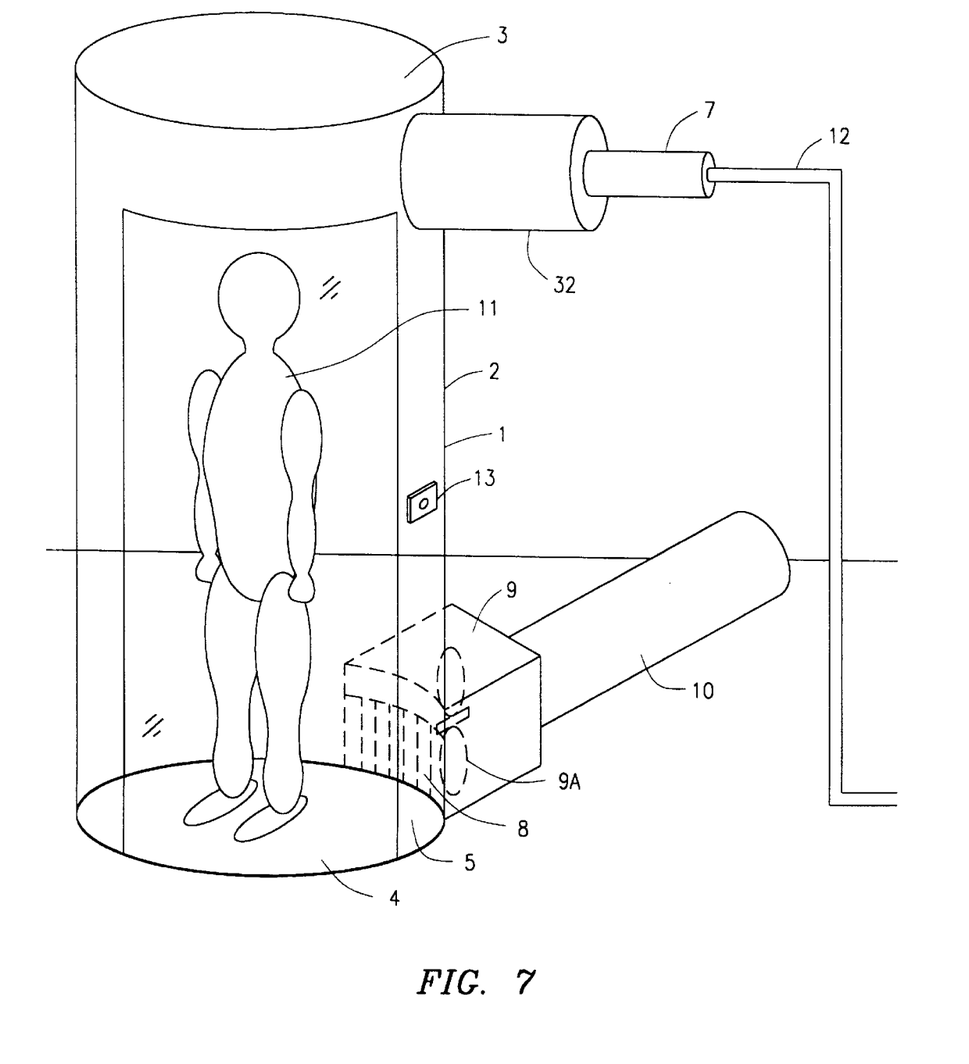

In another embodiment of the present invention, the misting solution is disbursed through the use of a misting chamber rather than moving nozzles. For example, FIG. 7 illustrates a booth 1 using a misting chamber 32. The booth 1 consists of walls 2, a ceiling 3 and door 5, all of which can be made of dielectric material. The booth 1 also includes a floor 4, possibly, made of a conductive material such as metal. Attached to the upper section of one of the walls 2 or to the ceiling 3, high enough to be above the head of any potential user of the booth, is a misting chamber 32 which consists of a cylinder made of a dielectric material open on the end attached to the wall 2 or ceiling 3 enclosed on the end away from the wall 2 or ceiling 3. Attached to the closed end of the misting chamber 32 is at least one electrostatic nozzle 7 which is part of the electrostatic misting apparatus 12 used to create the electrostatic mist. Attached to the base of wall 2 is an exhaust housing 9 which is opened on the end attached to the wall 2 and connect to an exhaust conduit on the end away from the wall 2. The exhaust housing 9 is made of a dielectric material and contains an exhaust filter 8 on the open end attached to wall 2 and exhaust bin 9A. When the booth 1 is in operation, user 11 would be inside the booth 1 standing barefoot on the floor, which can be constructed of a conductive material that is grounded—thereby grounding the user 11.

In another embodiment of the present invention, a device is included that produces a negative electrostatic charge on the walls 2 of the booth. By producing a negative electrostatic charge on the walls of the booth, the charged particles of the misting solution are repelled from the walls 2 with greater force, thereby increasing the efficiency of moving the charged droplets to the center of the booth. Additionally, a perforated inner wall layer (not illustrated) can be added to the misting booth and air can be forced outward through the perforations toward the center of the booth, thereby forcing the charged droplets away from the wall and toward the center of the booth. Furthermore, the booth shape can be altered to include circular, hexagonal, octagonal, or even rectangular shapes, and one embodiment of the present invention includes misting nozzles at different sides of the booth, possibly, with the user positioned between them. By positioning the misting nozzles in this fashion, the user can be coated in his entirety without rotating. Alternatively, the misting nozzles can be spaced throughout the booth to provide even coating.

Those skilled in the art can readily recognize that numerous variations and substitutions may be made in the invention, its use and its configuration to achieve substantially the same results as achieved by the embodiments described herein. Accordingly, there is no intention to limit the invention to the disclosed exemplary forms. Many variations, modifications and alternative constructions will fall within the scope and spirit of the disclosed invention as expressed in the claims.

What is claimed:

1. An apparatus for electrostatically coating a human with a coating composition, the apparatus comprising:
   an enclosure;
   a mount positioned on the enclosure;
   an electrostatic nozzle connected to the mount, the electrostatic nozzle for passing the coating composition; and
   means inside the enclosure for electrically grounding the human;
      wherein the coating composition passed through the electrostatic nozzle is depositable upon the human.

2. The apparatus of claim 1 wherein the enclosure comprises:
   a first wall wherein the mount is positioned on the first wall; and
   a second wall positioned substantially opposite the first wall, the second wall including a portion curved about an axis.

3. The apparatus of claim 2, wherein the portion of the second wall curved about an axis forms a parabolic curve.

4. The apparatus of claim 2, wherein the portion of the second wall curved about an axis forms an elliptical curve.

5. The apparatus of claim 2, wherein the portion of the second wall curved about an axis forms a circular curve.

6. The apparatus of claim 1, wherein the enclosure has a circular cross section corresponding to a vertical plane intersecting the enclosure.

7. The apparatus of claim 1, wherein the enclosure comprises:

a door for permitting the human to enter the enclosure.

8. The apparatus of claim 1, wherein the grounding connection comprises is a grounding plate positionable for contact with the human.

9. The apparatus of claim 1, further comprising:

a fluid path connected to the electrostatic nozzle, the fluid path for carrying the coating composition to the electrostatic nozzle.

10. The apparatus of claim 9, further comprising:

a reservoir connected to the fluid path, the reservoir for storing the coating composition.

11. The apparatus of claim 1, wherein the enclosure comprises a dielectric material.

12. The apparatus of claim 1, further comprising:

means to electrically charge the enclosure.

13. The apparatus of claim 1, wherein the electrostatic nozzle is configurable to pass an atomized and electrically charged coating composition.

14. The apparatus of claim 1, further comprising an exhaust means placed proximate to the enclosure, the exhaust means for at least removing a portion of the coating composition passed by the electrostatic nozzle.

15. The apparatus of claim 14, wherein the exhaust means comprises an exhaust fan.

16. The apparatus of claim 14, wherein the exhaust means is substantially formed of a dielectric material.

17. The apparatus of claim 1, wherein the mount comprises a mount moving means secured to the mount, wherein the mount is movable by the mount moving means such that the mount and the electrostatic nozzle are movable.

18. The apparatus of claim 17, wherein the mount moving means comprises a worm drive.

19. The apparatus of claim 17, wherein the mount moving means is configured to move the mount in a vertical direction.

20. The apparatus of claim 17, wherein the mount moving means is configured to pivot the mount in a vertical plane.

21. The apparatus of claim 17, wherein the mount moving means is configured to pivot the mount in a horizontal plane.

22. The apparatus of claim 1, wherein the electrostatic nozzles first electrostatic nozzle and the mount is a first mount, the apparatus further comprising:

a second mount positioned on the enclosure; and a second electrostatic nozzle connected to the second mount, the second electrostatic nozzle for passing the coating composition.

23. The apparatus of claim 22, wherein the second mount is located separate from the first mount.

24. The apparatus of claim 1, further comprising:

a misting chamber positioned adjacent to the enclosure, the misting chamber for substantially directing the coating composition into the enclosure.

25. The apparatus of claim 1, further comprising:

a compressed air supply connected to the electrostatic nozzle, the compressed air supply for providing compressed air to the electrostatic nozzle.

26. The apparatus of claim 25, wherein the compressed air supply comprises an air compressor.

27. The apparatus of claim 25, wherein the compressed air supply comprises an air tank.

28. The apparatus of claim 25, further comprising:

an air flow regulator for regulating the pressure of the compressed air provided to the electrostatic nozzle.

29. The apparatus of claim 1, further comprising:

a conduit connected to the electrostatic nozzle, the conduit for receiving compressed air for use by the electrostatic nozzle.

30. The apparatus of claim 1, further comprising:

a reservoir for storing the coating composition;

a coating composition line connected to the reservoir and the electrostatic nozzle, the coating composition line for carrying the coating composition from the reservoir to the electrostatic nozzle; and a compressed air intake connected to the reservoir, the compressed air intake for receiving compressed air.

31. A method for applying a coating composition to a human, the method comprising the steps of;

providing a coating solution;

providing an electrostatic nozzle for spraying the coating solution;

atomizing the coating solution;

electrically charging the coating solution;

grounding a floor upon which a human stands;

directing the electrically charged and atomized coating solution towards the human; and depositing at least a portion of the electrically charged and atomized coating solution on the human.

32. The method of claim 31, wherein the step of atomizing occurs before the step of electrically charging.

33. The method of claim 31, wherein the step of electrically charging occurs before the step of atomizing.

34. The method of claim 31, further comprising:

the step of electrically attracting the coating solution towards the human.

35. The method of claim 31, further comprising the steps of:

providing an enclosure for enclosing the human;

electrically repelling the coating solution from at least a portion of the enclosure.

36. The method of claim 35, further comprising the steps of:

extracting at least a portion of the coating solution from the enclosure, the extracted at least a portion of the coating solution not being deposited on the human.

37. The method of claim 33, further comprising the steps of:

moving the electrostatic nozzle.

38. The method of claim 37, wherein the step of moving the electrostatic nozzle includes the step of moving the electrostatic nozzle in a vertical direction.

39. The method of claim 37, wherein the step of moving the electrostatic nozzle includes the step of oscillating the electrostatic nozzle.

40. The method of claim 39, wherein the step of moving the electrostatic nozzle includes the step of oscillating the electrostatic nozzle in a vertical plane.

* * * * *

UNITED STATES PATENT AND TRADEMARK OFFICE
CERTIFICATE OF CORRECTION

PATENT NO. : 6,387,081 B1
DATED : May 14, 2002
INVENTOR(S) : Troy H. Cooper

It is certified that error appears in the above-identified patent and that said Letters Patent is hereby corrected as shown below:

Column 9,
Line 51, replace "nozzles first" with -- nozzle is a first --

Column 10,
Line 23, replace "comprising the steps of;" with -- comprising the steps of: --

Signed and Sealed this

Seventh Day of January, 2003

JAMES E. ROGAN
*Director of the United States Patent and Trademark Office*